United States Patent [19]

Klee et al.

[11] Patent Number: 5,346,622

[45] Date of Patent: Sep. 13, 1994

[54] HYDROCARBON CLASS SEPARATION AND QUANTITATION BY SPLIT COLUMN EFFLUENT ANALYSIS

[75] Inventors: Matthew S. Klee; Mu Zou Wang, both of Wilmington, Del.

[73] Assignee: Hewlett-Packard Company, Palo Alto, Calif.

[21] Appl. No.: 26,385

[22] Filed: Mar. 4, 1993

[51] Int. Cl.⁵ .......................................... B01D 15/08
[52] U.S. Cl. ................................. 210/659; 210/656; 210/198.2; 436/161; 585/825
[58] Field of Search .................... 210/635, 656, 198.2, 210/101, 96.1, 659; 436/161; 585/825; 73/61.56, 61.58

[56] References Cited

U.S. PATENT DOCUMENTS

| | | | |
|---|---|---|---|
| 3,458,437 | 7/1969 | Ouano | 210/659 |
| 3,496,763 | 2/1970 | Broerman | 210/656 |
| 3,725,232 | 4/1973 | Pretorius | 210/656 |
| 3,935,097 | 1/1976 | Roof | 210/659 |
| 4,016,074 | 4/1977 | Porter | 210/659 |
| 4,137,161 | 1/1979 | Shimada | 210/198.2 |
| 4,204,952 | 5/1980 | Snyder | 210/659 |
| 4,446,105 | 5/1984 | Dinsmore | 210/659 |
| 4,454,043 | 6/1984 | Ting | 210/659 |
| 4,478,720 | 10/1984 | Perrut | 210/659 |
| 4,479,380 | 10/1984 | Novotny | 210/656 |
| 4,699,718 | 10/1987 | Jones | 210/659 |
| 4,814,089 | 3/1989 | Kumar | 210/659 |
| 4,840,730 | 6/1989 | Saxena | 210/198.2 |
| 5,009,778 | 4/1991 | Nickerson et al. | 210/198.2 |
| 5,094,741 | 3/1992 | Frank et al. | 210/198.2 |
| 5,133,859 | 7/1992 | Frank et al. | 210/198.2 |
| 5,139,681 | 8/1992 | Cortes | 210/659 |
| 5,151,178 | 9/1992 | Nickerson et al. | 210/198.2 |
| 5,178,767 | 1/1993 | Nickerson et al. | 210/656 |
| 5,180,487 | 1/1993 | Saito | 210/659 |
| 5,234,599 | 8/1993 | Cortes | 210/659 |

OTHER PUBLICATIONS

Standard Test Method for Determination of Aromatic Content of Diesel Fuels by Supercritical Fluid Chromatography, Designation: D 5186-91, Annual Book of ASTM Standards, vol. 05.01, published Dec. 1991, pp. 855-857.

*Primary Examiner*—Ernest G. Therkorn
*Attorney, Agent, or Firm*—Richard F. Schuette

[57] ABSTRACT

Methods of separating and classifying the relative amounts of two or more classes of hydrocarbon molecules in a sample are disclosed wherein an input stream comprising a mobile phase and the sample is injected into a chromatographic column, and an effluent stream exiting a chromatographic column is split into a first effluent stream and a second effluent stream. The mass of carbon in each of the classes of hydrocarbons in the first effluent stream is determined, preferably using a flame ionization detector, and the second effluent stream is directed through a variable restrictor, allowing the pressure and mass flow rate of the input stream to be independently controlled and improved results obtained. In a preferred embodiment the present invention also includes identifying the hydrocarbon molecules in the second effluent stream in order to verify the analysis or provide additional data, preferably by using an ultraviolet detector. The present invention is most preferably used to analyze the aromatic hydrocarbons in a sample of diesel fuel.

10 Claims, 1 Drawing Sheet

HYDROCARBON CLASS SEPARATION AND QUANTITATION BY SPLIT COLUMN EFFLUENT ANALYSIS

The present invention relates to analytical chemistry, and in particular, the present invention provides methods and apparatus for separating and quantifying classes of hydrocarbons in a sample.

BACKGROUND OF THE INVENTION

A number of chromatographic techniques are known for separating the components of a sample. In packed column chromatography, a mobile phase fluid and a sample flow through a column containing a stationary phase, which is chosen to retain specific components of the sample. Supercritical fluid chromatography (SFC) uses a supercritical fluid, usually carbon dioxide, as the mobile phase. The solvent power of the mobile phase in supercritical fluid chromatography is a linear function of density, which is in turn related to pressure. However, in systems such as SFC systems that use compressible fluids at pressures above atmospheric (ambient), the pressure of the system is coupled to the mass flow rate.

The problems caused by the coupling between pressure and mass flow rate in supercritical fluid systems and their solution are explained in detail in commonly-assigned U.S. Pat. Nos. 5,133,859; 5,094,741 and U.S. patent application Ser. No. 804,155 filed Dec. 6, 1991—Frank et al., which are all incorporated herein by reference. Frank et al. teach that mass flow rate and pressure can be "decoupled" and independently controlled by providing a variable orifice restrictor downstream from, e.g., the column of a chromatographic instrument or the extraction chamber of an extraction instrument. Variable orifice restrictors and their use are disclosed in commonly-assigned U.S. Pat. Nos. 5,009,778; 5,151,178 and 5,178,767—Nickerson et al. which are all incorporated herein by reference. As used herein, "variable restrictors" refer to variable orifice restrictors such as those disclosed in the Frank and Nickerson patents, as well as other types of restrictors in which the degree of restriction is changed by varying the size of an orifice, occluding an orifice, changing other physical characteristics of an orifice or interchanging and selecting fixed orifices of varying sizes within a valve or similar device.

A specific application of supercritical fluid chromatography is the analysis of the aromatic content of diesel fuels using packed columns and a flame ionization detector (FID). The test method is set forth in ASTM D518691, published by the American Society for Testing and Materials, 1916 Race Street, Philadelphia, Pa. (USA) 19103-1187, which is incorporated herein by reference. The above-referenced ASTM method is generally applicable to many different types of petroleum and chemical samples where the goal is to determine the relative amounts of different classes of hydrocarbons. Basically, saturated hydrocarbons are separated from aromatic hydrocarbons in an SFC column and the flame ionization detector provides a signal based on the mass of carbon in each class of hydrocarbon.

The ASTM method specifies a fixed restrictor at the end of the SFC column to maintain the necessary pressure for supercritical fluid chromatography. However, there are several disadvantages to this configuration. First, fixed restrictors clog, changing retention time and the response of the flame ionization detector. Also, since every restrictor is different, no two sets of analysis equipment will have equivalent retention times, thereby introducing an uncertainty into the test method. Additionally, as explained above, in a fixed restrictor system, flow rate through the column is directly related to the pressure and the restrictor, so optimization and maintenance of chromatographic conditions is very difficult.

Another problem with the ASTM method is that the response of flame ionization detectors becomes nonlinear and non-uniform for the different classes of hydrocarbons as the flow the supercritical fluid mobile phase becomes too large. This limits the size of columns that can be used. Typically, the larger the column size, the larger the flow to the flame ionization detectors. Thus, in this type of system, smaller columns are less problematic than larger columns. It would be desirable to be able to control the flow rate to permit the use of columns having a larger inner diameter than typical SFC columns.

Finally, even though the flame ionization detector provides a signal representing the mass of the carbon atoms in the molecule, some diesel fuels with relatively the same amount of aromatic compounds perform quite differently in engines. Therefore, the flame ionization detector signal alone is not sufficient to differentiate all the diesel fuels being tested. Accordingly, it would be further desirable to provide a system wherein additional analytical techniques or instruments can be incorporated to simultaneously analyze the effluent stream from the SFC column to more accurately characterize the sample.

SUMMARY OF THE INVENTION

It has now been found, however, that the shortcomings of the prior art methods of separating and classifying the relative amounts of two or more classes of hydrocarbon molecules in a sample can be overcome. The present invention discloses methods wherein an input stream comprising a mobile phase, preferably a supercritical fluid, and the sample is injected into a chromatographic column at predetermined conditions of pressure and flow rate, and an effluent stream exiting the chromatographic column is split into a first effluent stream and a second effluent stream. Preferably, first effluent stream has a substantially smaller mass flow rate than the second effluent stream, and most preferably, comprises less than 5% of the input stream. By determining the mass of carbon in each of the classes of hydrocarbons in the first effluent stream, preferably using a flame ionization detector, and directing the second effluent stream through a variable restrictor, the pressure and mass flow rate of the input stream can be independently controlled while improved results are obtained. In a preferred embodiment the method includes the further step of identifying the hydrocarbon molecules in the second effluent stream in order to verify the analysis or provide additional data. Preferably, the second effluent stream is directed into a detector, such as an ultraviolet detector, for this purpose. In a most preferred embodiment, the methods of the present invention are used with a sample comprised of diesel fuel, and the classes of hydrocarbons comprise saturated and aromatic hydrocarbons.

The present invention also discloses preferred embodiments of apparatus for separating and classifying the relative amounts of two or more classes of hydrocarbon molecules in a sample in accordance with the above-described methods. Preferably, a chromatograph for producing an effluent stream, a detector receiving a first portion of the effluent stream, and a variable orifice restrictor receiving a second portion of the effluent stream are provided. The variable restrictor permits the independent control the pressure and flow rate of the input stream. The chromatograph is most preferably a supercritical fluid chromatograph that includes a column packed with an adsorbent such as silica; the column most preferably has an internal diameter of between 1 to 5 millimeters (mm). In certain embodiments, an apparatus for identifying the hydrocarbon molecules in the second effluent stream, such as a multi-wavelength ultraviolet detector is also included.

The variable orifice restrictors used in the present invention may be of any of a number of different types. For example, the restrictor may comprise an axially moveable pin to restrict mass flow by varying the size of an orifice. Mass flow rate may also be varied by selecting an orifice plate comprising a fixed orifice and inserting the orifice plate into a variable restrictor device.

DETAILED DESCRIPTION OF THE PREFERRED EMBODIMENTS

Figure 1:
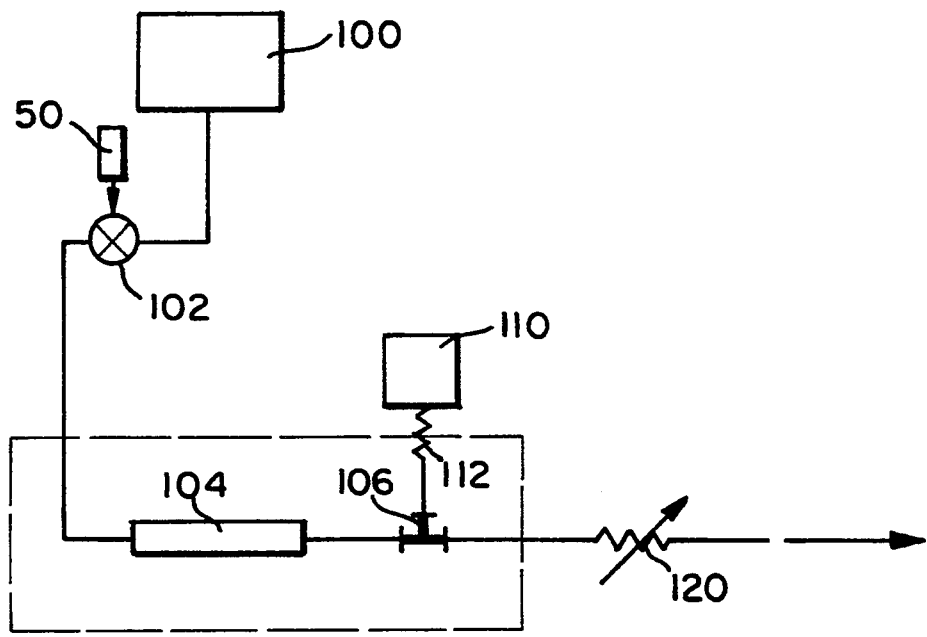
FIG. 1 is a schematic representation of the apparatus of the present invention.

Referring now to FIG. 1, there is shown a schematic representation of an apparatus made in accordance with the present invention. Typically, a source of the mobile phase fluid, such as a pump 100 is connected to an injection valve 102 for introducing a sample 50 to be analyzed into a chromatographic column 104. The flow into the column 104 forms an input stream, that flows through the chromatographic column 104, which is packed with a stationary phase (not shown), that is most preferably comprised of an adsorbent such as silica and the sample is eluted by the mobile phase. Those of ordinary skill will understand that the column 104 requires surrounding instrumentation and controls and will typically be resident within a chromatograph instrument, such as the HP G1205A, manufactured by Hewlett-Packard, Little Falls, Del. (USA). However, it will also be understood that other suitable analytical instruments for isolating aromatic compounds or other classes of hydrocarbons can be used in conjunction with the present invention.

After the input stream has flowed through the chromatographic column 104, an effluent stream will be created. In the present invention, the effluent stream is split into at least two streams at a tee 106, as shown in FIG. 1. It will be appreciated that the effluent stream can also be split into multiple (e.g. three or more) streams in certain embodiments. In the embodiment illustrated, a first effluent stream is connected to a flame ionization detector 110 and, as explained above, produces a signal indicative of the mass of carbon in each class of hydrocarbon compounds in the sample. As known to those of skill in the art and specified by the ASTM method D5186-91 described above and incorporated herein by reference, the inlet to the flame ionization detector 110 includes a fixed restrictor 112. A second effluent stream flows from the tee 106 to a variable restrictor 120, which permits the pressure and flow rate in the system to be "decoupled" and separately controlled in accordance wit the present invention. In addition to permitting pressure and flow rate to be separately controlled, the variable restrictor 120 increases retention time reproducibility because it is adjustable and relatively immune to clogging, unlike the fixed restrictor specified by the ASTM method which clogs, causing changes in retention time.

The benefits of the present invention are derived from the splitting the column effluent into two streams. Preferably, the two streams are not equal, and the fraction of the effluent which flows to the flame ionization detector 110 is a function of the pressure at the exit of the column and the resistance of the fixed restrictor 112 at the inlet of the flame ionization detector 110. Preferably, the effluent flow to the flame ionization detector 110 is small relative to the flow continuing to the variable restrictor 120. In a most preferred embodiment, less than five percent (5%) of the flow exiting the column 104 is directed to the flame ionization detector 110. By splitting the effluent steam the flow rate to the flame ionization detector 110 is reduced, and thus more accurate response for different hydrocarbon classes is obtained. Additionally, even if the fixed restrictor 112 that must be used with the flame ionization detector 110 becomes clogged, the split effluent configuration makes the analysis more reliable because the majority of the effluent flow is directed to the variable restrictor and the retention time of the peaks are insignificantly affected.

In preferred embodiments of the present invention, the chromatographic column 104 is larger than the columns typically used in supercritical fluid chromatography and are preferably the standard columns used for high pressure liquid chromatography (HPLC). Splitting the effluent steam allows such larger diameter columns to be operated at optimum flow rates. The column 104 used in the present invention most preferably inner diameter between approximately 1 to 5 millimeters (mm). The larger columns are more rugged and have longer lifetimes, and are packed more efficiently than smaller size columns typically required for supercritical fluid chromatographs that direct all of the column flow to the flame ionization detector 110. Although larger columns have more inherent benefits, 1 mm columns are commonly used in supercritical fluid chromatography and are also useful with the present invention.

Figure 2:
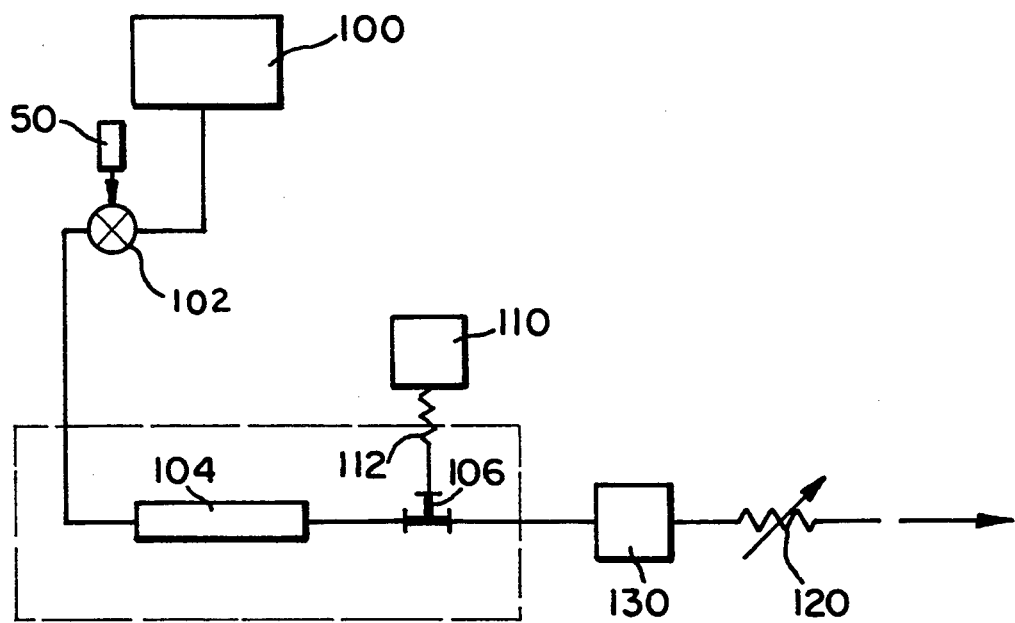
FIG. 2 is a schematic representation of an alternate embodiment of the apparatus of the present invention.

Referring now to FIG. 2, another advantage created by splitting the effluent stream can be seen. As shown in FIG. 2, a multi-wavelength ultraviolet (UV) detector 130 can be incorporated into the system of the present invention. This device allows the simultaneous verification of the accuracy of integration of the flame ionization detector chromatogram and differentiation between samples of similar aromatic content. In addition to the multi-wavelength detector 130 described with respect to FIG. 2, it will be appreciated that other types of analytical devices could be incorporated into the system of the present invention in a similar matter. For example, an infrared detector or a refractive index detector could be used to identify the constituents of the effluent stream to correlate the results obtained from the flame ionization detector 110. Also, as mentioned above, additional streams of effluent may be formed in certain embodiments; in the case where one of these additional "splits" is formed before the variable restrictor 120, this additional stream would be analyzed using a mass spectrometer.

Although the present invention has been described with reference to a specific type of analysis using specific apparatus, upon review of the information set forth above that will make numerous modifications and adaptations of the present invention readily apparent to those of ordinary skill in the art. A wide variety of analytical procedures can be improved by incorporating a variable restrictor into the effluent stream exiting a chromatograph or extraction chamber. Accordingly, reference should be made to the appended claims in order to determine the full scope of the present invention.

What is claimed is:

1. A method of separating and classifying the relative amounts of two or more classes of hydrocarbon molecules in a sample, comprising the steps of:

injecting an input stream comprising a mobile phase and the sample into a chromatograph at predetermined conditions of pressure, temperature and flow rate;

splitting an effluent stream exiting the chromatograph into a first effluent stream and a second effluent stream;

determining the mass of carbon in each of the classes of hydrocarbons in the first effluent stream;

directing the second effluent stream through a variable restrictor; and adjusting the variable restrictor to independently control the pressure and flow rate of the input stream.

2. The method of claim 1, wherein the mobile phase comprises a supercritical fluid.

3. The method of claim 1, wherein the step of determining the mass of carbon comprises directing the first effluent stream into a flame ionization detector.

4. The method of claim 1, further comprising the step of identifying the hydrocarbon molecules in the second effluent stream.

5. The method of claim 4, wherein the step of identifying the hydrocarbon molecules comprises directing the second effluent stream into an ultraviolet detector.

6. The method of claim 1, wherein the step of adjusting the variable restrictor comprises axially moving a pin to restrict mass flow by varying the size of an orifice.

7. The method of claim 1, wherein the step of adjusting the variable restrictor comprises selecting an orifice plate comprising a fixed orifice and inserting the orifice plate into the variable restrictor.

8. The method of claim 7, wherein the first effluent stream comprises less than 5% of the input stream.

9. The method of claim 1, wherein the step of splitting the effluent stream exiting the column creates a first effluent stream having a substantially smaller mass flow rate than the second effluent stream.

10. The method of claim 1, wherein the sample comprises diesel fuel and the classes of hydrocarbons comprise saturated and aromatic hydrocarbons.

* * * * *